United States Patent
Dexter et al.

(10) Patent No.: US 9,253,981 B2
(45) Date of Patent: Feb. 9, 2016

(54) STABLE SUSPENSION CONCENTRATE FORMULATION FOR WATER-SOLUBLE COMPOUNDS

(75) Inventors: Robin W. Dexter, Yardley, PA (US); Hong Liu, Pennington, NJ (US)

(73) Assignee: FMC Corporation, Philadelphia, PA (US)

( * ) Notice: Subject to any disclaimer, the term of this patent is extended or adjusted under 35 U.S.C. 154(b) by 429 days.

(21) Appl. No.: 12/445,905

(22) PCT Filed: Oct. 16, 2007

(86) PCT No.: PCT/US2007/081506
§ 371 (c)(1),
(2), (4) Date: Jun. 1, 2009

(87) PCT Pub. No.: WO2008/067058
PCT Pub. Date: Jun. 5, 2008

(65) Prior Publication Data
US 2010/0197739 A1    Aug. 5, 2010

Related U.S. Application Data

(60) Provisional application No. 60/852,240, filed on Oct. 17, 2006.

(51) Int. Cl.
| | |
|---|---|
| A01N 43/40 | (2006.01) |
| A01P 7/04 | (2006.01) |
| A61K 47/02 | (2006.01) |
| A61K 47/38 | (2006.01) |
| A01N 51/00 | (2006.01) |

(52) U.S. Cl.
CPC ............... *A01N 43/40* (2013.01); *A01N 51/00* (2013.01); *A61K 47/02* (2013.01); *A61K 47/38* (2013.01); *A61L 2400/06* (2013.01)

(58) Field of Classification Search
CPC .... A61L 2400/06; A61K 47/02; A61K 47/38; A61K 9/0019
See application file for complete search history.

(56) References Cited

U.S. PATENT DOCUMENTS

| | | | |
|---|---|---|---|
| 4,804,399 A | 2/1989 | Albrecht et al. | |
| 5,889,088 A | 3/1999 | Kisuno et al. | |
| 2002/0155954 A1 | 10/2002 | Aven | |
| 2004/0118040 A1* | 6/2004 | Asrar et al. | 47/57.6 |
| 2005/0076686 A1 | 4/2005 | Tidow et al. | |
| 2006/0270559 A1* | 11/2006 | Maekawa et al. | 504/358 |
| 2007/0142439 A1 | 6/2007 | Morita et al. | |

FOREIGN PATENT DOCUMENTS

| | | |
|---|---|---|
| GB | 1434697 | 5/1976 |
| JP | 2001-342102 | 12/2001 |
| JP | 2002-087911 | 3/2002 |
| JP | 2002-179506 A | 6/2006 |
| WO | 2005104846 A1 | 11/2005 |
| WO | 2006/079079 A1 | 7/2006 |
| WO | 2006/127298 A2 | 11/2006 |

OTHER PUBLICATIONS

Kumulus DF Fungicide/Acaracide Technical Label, Arysta LifeScience, NA LLC.
Aria Insecticide Technical Label, FMC Corporation, Philadelphia, PA.
Credo SC Insecticide, Bayer Healthcare LLC, KS 66201, www.bayer-ah.com.
Pallas et al. Pesticide Formulations and Application Systems 16th vol. ASTM STP 1312, 1996.

* cited by examiner

*Primary Examiner* — Kyle Purdy
(74) *Attorney, Agent, or Firm* — FMC Corporation

(57) ABSTRACT

The present invention is directed to an insecticidal water based suspension concentrate formulation comprising a water-soluble insecticide selected from the group consisting of N-cyanomethyl-4-(trifluoromethyl)nicotinamide and (EZ)-1-(6-chloro-3-pyridylmethyl)-N-nitroimidazolidin-2-ylidineamine and at least one water-soluble salt selected from the group consisting of magnesium sulfate (hydrated and anhydrous forms) and sodium sulfate, wherein the water-soluble insecticide is present in an insecticidally effective amount and methods of use.

13 Claims, No Drawings

STABLE SUSPENSION CONCENTRATE FORMULATION FOR WATER-SOLUBLE COMPOUNDS

This application claims the benefit of U.S. Provisional Application No. 60/852,240, filed Oct. 17, 2006.

FIELD OF THE INVENTION

The present invention relates to the field of insecticides and chemical formulations. In particular, the invention provides a novel aqueous based insecticidal composition of a water-soluble insecticide that is physically stable.

BACKGROUND OF THE INVENTION

To enable the efficient elimination or controlling of unwanted insects in agriculture and related endeavors, it is desirable to use effective chemical insecticides on these unwanted pests. Formulations containing insecticides are desirable in agricultural and related endeavors in order to effectively distribute the active ingredient to the area that insect control is desired. Physical stability is most important in this type of formulation in order to ensure the small amount of the insecticide is fully effective. The production of a stable, water-based suspension concentrate formulation of a water-soluble insecticide is difficult due to the formation of large crystals in the process known as Ostwald ripening. These large crystals may not dissolve completely when diluted with water resulting in clogged spray apparatus and uneven pesticidal applications. Maintaining a stable suspension concentrate with a uniform particle size distribution (i.e. no large crystals) is most important for this type of formulation in order to prevent settling of particles during storage.

SUMMARY OF THE INVENTION

In accordance with the present invention, it has now been found that a physically stable, water based suspension concentrate composition containing a water-soluble insecticide is formed, without the formation of large crystals, by the addition of at least one or more neutral water-soluble salts. Specifically, the present invention is directed to a stable insecticidal composition comprising a water-soluble insecticide selected from the group consisting of N-cyanomethyl-4-(trifluoromethyl)nicotinamide and (EZ)-1-(6-chloro-3-pyridylmethyl)-N-nitroimidazolidin-2-ylidineamine and at least one water-soluble salt selected from the group consisting of magnesium sulfate (hydrated and anhydrous forms) and sodium sulfate.

DETAILED DESCRIPTION OF THE INVENTION

The present invention is directed to a novel water-based suspension concentrate composition comprising a water-soluble insecticide selected from the group consisting of N-cyanomethyl-4-(trifluoromethyl)nicotinamide and (EZ)-1-(6-chloro-3-pyridylmethyl)-N-nitroimidazolidin-2-ylidineamine and at least one water-soluble salt selected from the group consisting of magnesium sulfate (hydrated and anhydrous forms) and sodium sulfate, wherein the water-soluble insecticide is present in an insecticidally effective amount. The insecticidal composition may further comprise additional components selected from one or more surfactants, an antifoam agent, a preservative, a thickener or suspending agent and water.

The water-soluble insecticide is selected from the group consisting of flonicamid, the common name for N-cyanomethyl-4-(trifluoromethyl)nicotinamide and imidacloprid, the common name for (EZ)-1-(6-chloro-3-pyridylmethyl)-N-nitroimidazolidin-2-ylidineamine. The water-soluble insecticide can be present in a concentration of from 1% to 40% by weight, preferably from 10% to 25% by weight based upon the total weight of all components in the composition.

The neutral water-soluble salt is selected from the group consisting of magnesium sulfate (hydrated and anhydrous forms) and sodium sulfate. A preferred salt is magnesium sulfate. The neutral water-soluble salt may be present in a concentration of from 1% to 35% by weight, preferably from 10% to 30% by weight based upon the total weight of all components in the composition.

The term "surfactant" is used in the broad sense to include materials which may be referred to as dispersing agents and wetting agents, and the surfactant component may comprise one or more dispersing or wetting agents provided that the dispersing or wetting agent is soluble when added to an aqueous solution containing from 10% to 20% of the water-soluble salt.

Preferably the surfactant component is comprised of at least one wetting agent such as those selected from sodium alkyl naphthalene sulfonates and alkyl polyglycosides; or at least one dispersing agent such as those selected from naphthalene sulfonates and lignosulfonates, or a mixture of wetting and dispersing agents. The total surfactant component can comprise from 0.1% to 10% and preferably from 1% to 5% by weight based upon the total weight of all components in the composition.

Examples of surfactants preferred as wetting agents for the water based suspension concentrate composition of the present invention include MORWET® EFW (Akzo Nobel Corporation) and AGRIMUL PG 2076 (AGRIMUL is a trademark of Cognis Corporation). The most preferred wetting agent is AGRIMUL PG 2076.

Examples of dispersants preferred for the water based suspension concentrate formulation of the present invention include REAX® 88B and POLYFON® O (both available from MeadWestvaco Corporation) and MORWET®D-425 (Akzo Nobel Corporation). The most preferred dispersant is MORWET® D-425.

The anti-foam agent can be an alkylcyclotetrasiloxane, preferably an octamethylcyclotetrasiloxane, silicone emulsion, for example, DOW CORNING® AF Emulsion (Dow Corning Corporation). The anti-foam agent can be present in an amount of from 0.001% to 1% by weight of all the components in the total formulation.

The preservative can be an isothiazolone mixture, for example, KATHON® CG/ICP preservative or LEGEND® MK preservative (Rohm and Haas Corporation). The preservative can be present in an amount of from 0.001% to 1% by weight of all the components in the total formulation.

The thickener or suspending agent can be a xanthan gum, for example, KELZAN® S (CP Kelco Company), or a magnesium alumino silicate, for example, ACTI-GEL® 208 (Active Minerals Company LLC). The thickener or suspending agent can be present in the amount of from 0.01% to 1% by weight of all the components in the total formulation.

Water is used as a diluent and preferably is purified water, for example, deionized or distilled water, and is present in an amount that would dilute the active ingredient to a desired concentration.

A preferred embodiment of the invention is an insecticidal water based suspension concentrate composition wherein N-cyanomethyl-4-(trifluoromethyl)nicotinamide is present in an amount of from 15% to 25%, magnesium sulfate is present in an amount of from 10% to 30%, the surfactant component is present in an amount of 1% to 5%, the antifoam agent is present in an amount of from 0.001% to 1%, the preservative is present in the amount of from 0.001% to 1%, the thickener or suspending agent is present in an amount of from 0.01% to 1.0% and water is present in an amount sufficient to provide the desired concentration of the active ingredient, wherein all %'s are % by weight based upon the total weight of all the components in the formulation.

The terms "ambient temperature" and "room temperature" as utilized herein shall generally mean any suitable temperature found in a laboratory or other working quarter, and is generally not below about 15° C. nor above about 30° C.

The composition of the present invention is further illustrated by the examples below. The examples serve only to illustrate the invention and should not be interpreted as limiting since further modifications of the disclosed invention will be apparent to those skilled in the art. All such modifications are deemed to be within the scope of the invention as defined in the claims. Particle size and distribution was performed using a particle size distribution analyzer (Horiba Particle Scattering Particle Size Distribution Analyzer LA-910).

Example 1

This Example Illustrates One Protocol for the Preparation of a Water Based Suspension Concentrate Composition Containing N-cyanomethyl-4-(trifluoromethyl)nicotinamide, a Formulation of the Present Invention, Formulation Code (F1)

To a solution of 4.00 grams of MORWET® D-425 dissolved in 113.04 grams of de-ionized water in a 400 mL bowl of a vertical bead mill (fixed with a mechanical agitator, using stainless steel beads 3 mm in diameter) was added in succession with stirring, 4.00 grams of AGRIMUL PG-2076, 0.10 gram of Dow AF, 10.00 grams of a 1% aqueous solution of KELZAN® S, and 28.26 grams of anhydrous magnesium sulfate. The mixture was allowed to cool to room temperature and 40.60 grams of N-cyanomethyl-4-(trifluoromethyl)nicotinamide (technical grade, 98.5% purity by weight, particle size of less than 200 microns) was added. The mixture was milled for 2.5 hours at a speed of 100 RPM and a temperature of 20° C. The resulting cream colored mixture was filtered to remove the stainless steel beads.

Example 2

This Example Illustrates One Protocol for the Preparation of a Water Based Suspension Concentrate Composition Containing N-cyanomethyl-4-(trifluoromethyl)nicotinamide and a Preservative, a Formulation of the Present Invention, Formulation Code (F2)

To a solution of MORWET® D-425 (2.20% by weight) dissolved in de-ionized water (36.28% by weight) in the bowl of a vertical bead mill (fixed with a mechanical agitator, using stainless steel beads 3 mm in diameter) was added in succession with stirring, AGRIMUL PG-2076 (0.20% by weight), DOW CORNING® AF (0.20% by weight), LEGEND® MK (0.20% by weight) and magnesium sulfate heptahydrate (30.72% by weight). The mixture was allowed to cool to room temperature and N-cyanomethyl-4-(trifluoromethyl)nicotinamide (15.20% by weight, technical grade, 98.5% purity by weight, particle size of less than 200 microns) was added. The mixture was milled at a speed of 100 RPM and a temperature of 20° C. until a particle size of less than 20 microns was obtained. A 1% aqueous solution of KELZAN® S (15.00% by weight) was added and the mixture was stirred until homogenous. The resulting light beige colored mixture was filtered to remove the stainless steel beads.

Example 3

This Example Illustrates One Protocol for the Preparation of a Water Based Suspension Concentrate Composition Containing (EZ)-1-(6-chloro-3-pyridylmethyl)-N-nitroimidazolidin-2-ylidineamine, a Formulation of the Present Invention, Formulation Code (F3)

In a manner similar to Example 1 the formulation consisting of MORWET® D-425 (2.20% by weight), de-ionized water (49.3% by weight), anhydrous magnesium sulfate (15.5% by weight) a 1% aqueous solution of KELZAN® S (18.0% by weight) and (EZ)-1-(6-chloro-3-pyridylmethyl)-N-nitroimidazolidin-2-ylidineamine (15.0% by weight) was produced.

Example 4

This Example Illustrates One Protocol for Testing the Stability of a Water Based Suspension Concentrate Formulation The filtrates from the examples above were transferred into storage bottles and the bottles were sealed. One bottle from each example was stored in an oven at 54° C. and the remaining bottles were stored at room temperature. The elevated temperature and room temperature samples were analyzed at periodic intervals for the presence of large crystals, uniformity of the formulation and stability of particle distribution.

Table 1 below sets forth the stability data of these formulations at the indicated time periods at room temperature and at elevated temperatures.

TABLE 1

Stability Data for the Formulations of the Present Invention

| Formulation Code (F#) | Storage Time (Weeks) | Storage Temperature (° C.) | Particle Size (microns) 90% distribution | Particle Size (microns) 50% distribution | Syneresis | Sedimentation Present | % Separation When Diluted With Water (2 Hour) | % Separation When Diluted With Water (4 Hour) |
|---|---|---|---|---|---|---|---|---|
| (F1) | 0 | 23 | NCG* | NCG* | none | none | 0 | 0 |
| (F1) | 2 | 54 | NCG* | NCG* | slight | none | 0 | 0 |
| (F2) | 0 | 23 | 10.5 | 6.2 | none | none | 0 | 0 |
| (F2) | 12 | 54 | 12.7 | 7.1 | none | none | 0 | 0 |

TABLE 1-continued

Stability Data for the Formulations of the Present Invention

| Formulation Code (F#) | Storage Time (Weeks) | Storage Temperature (° C.) | Particle Size (microns) 90% distribution | Particle Size (microns) 50% distribution | Syneresis | Sedimentation Present | % Separation When Diluted With Water (2 Hour) | % Separation When Diluted With Water (4 Hour) |
|---|---|---|---|---|---|---|---|---|
| (F3) | 0 | 23 | NCG* | NCG* | none | none | 0 | 0 |
| (F3) | 2 | 54 | NCG* | NCG* | none | none | 0 | 0 |

*NCG = No Crystal Growth, microscopic analysis at 400×.

Example 5

Solubility of N-cyanomethyl-4-(trifluoromethyl)nicotinamide in Salt Solutions

In order to determine the effectiveness of a salt to decrease the solubility of N-cyanomethyl-4-(trifluoromethyl)nicotinamide in aqueous solutions, the following tests were conducted:

A salt solution consisting of two grams of a salt dissolved in ten grams of water was prepared. Fifty milligrams of N-cyanomethyl-4-(trifluoromethyl)nicotinamide was added and the resulting mixture was subjected to sonication until all the N-cyanomethyl-4-(trifluoromethyl)nicotinamide had dissolved. The solutions were allowed to stand at ambient temperature for about 18 hours. Each solution was filtered and the filtrate was analyzed by HPLC to determine the amount of N-cyanomethyl-4-(trifluoromethyl)nicotinamide which remained dissolved in the water. An experiment in which no salt was added was included as a control.

Table 2 below summarizes the results obtained from these solubility tests.

TABLE 2

Solubility of N-cyanomethyl-4-(trifluoromethyl)nicotinamide in Salt Solutions

| Salt employed in test | Amount of N-cyanomethyl-4-(trifluoromethyl)nicotinamide in Salt Solutions After Filtration |
|---|---|
| Control | 50.0 mg |
| Magnesium Sulfate (Anhydrous) | 7.0 mg |
| Sodium Sulfate | 10.0 mg |

As can be seen in table 2, a concentration of 20% magnesium sulfate was effective in reducing the solubility of N-cyanomethyl-4-(trifluoromethyl)nicotinamide in an aqueous solution by over 90%. Likewise, sodium sulfate reduced the solubility of N-cyanomethyl-4-(trifluoromethyl)nicotinamide in an aqueous solution by 80%.

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A stable water-based suspension concentrate composition consisting of:
   a) a water-soluble insecticide present in a concentration of from 10% to 25% by weight based upon the total weight of all the components in the composition selected from the group consisting of N-cyanomethyl-4-(trifluoromethyl)nicotinamide and (EZ)-1-(6-chloro-3-pyridylmethyl)-N-nitroimidazolidin-2-ylideneamine;
   b) a neutral water-soluble salt selected from the group consisting of magnesium sulfate and sodium sulfate; wherein the salt is present in an amount of from 10% to 30% by weight based upon the total weight of all components in the composition;
   c) optionally a surfactant component;
   d) optionally an antifoam agent;
   e) optionally a preservative;
   f) optionally a thickener or a suspending agent; and
   g) water.

2. The composition of claim 1 wherein the water-soluble insecticide is N-cyanomethyl-4-(trifluoromethyl)nicotinamide.

3. The composition of claim 1 wherein the water-soluble insecticide is (EZ)-1-(6-chloro-3-pyridylmethyl)-N-nitroimidazolidin-2-ylideneamine.

4. A composition of claim 1 wherein the neutral water-soluble salt is magnesium sulfate and is present in an amount of from 10% to 30% by weight of all the components in the total composition.

5. The composition of claim 1 wherein the surfactant component is present in a concentration of from 1% to 5% by weight based on the total weight of all the components of the formulation.

6. The composition of claim 1 wherein the anti-foam agent is present in an amount of from 0.001% to 1% by weight of all the components in the total formulation.

7. The composition of claim 1 wherein the preservative is present in an amount of from 0.001% to 1% by weight of all the components in the total formulation.

8. The composition of claim 1 wherein the thickener or suspending agent is present in an amount of from 0.01% to 1.0% by weight of all the components in the total formulation.

9. A method for controlling unwanted insects comprising applying a composition of claim 1 to a locus where insects are present or are expected to be present.

10. A stable water-based suspension concentrate composition consisting of:
   a) N-cyanomethyl-4-(trifluoromethyl)nicotinamide present in an amount of from 10% to 25%;
   b) magnesium sulfate present in an amount of from 10% to 30%;
   c) a surfactant component present in a concentration of from 1% to 5%;
   d) an anti-foam agent present in an amount of from 0.001% to 1%;
   e) a preservative present in an amount of from 0.001% to 1%;

f) a thickener or suspending agent present in an amount of from 0.01% to 1.0%; and g) water;

wherein all % are % by weight based on the total weight of all the components in the formulation.

11. A method for controlling unwanted insects comprising applying a composition of claim 10 to a locus where insects are present or are expected to be present.

12. A stable water-based suspension concentrate composition consisting of:

g) (EZ)-1-(6-chloro-3-pyridylmethyl)-N-nitroimidazolidin-2-ylidineamine present in an amount of from 10% to 25%;

h) magnesium sulfate present in an amount of from 10% to 30%;

i) a surfactant component present in a concentration of from 1% to 5%;

j) an anti-foam agent present in an amount of from 0.001% to 1%;

k) a preservative present in an amount of from 0.001% to 1%;

l) a thickener or suspending agent present in an amount of from 0.01% to 1.0%; and m) water;

wherein all % are % by weight based on the total weight of all the components in the formulation.

13. A method for controlling unwanted insects comprising applying a composition of claim 12 to a locus where insects are present or are expected to be present.

* * * * *